(12) United States Patent
Haselby et al.

(10) Patent No.: US 10,349,975 B2
(45) Date of Patent: *Jul. 16, 2019

(54) TRI-FLUTED VASCULAR ACCESS NEEDLE (71) Applicant: Cook Medical Technologies LLC, Bloomington, IN (US)

(72) Inventors: Kenneth A. Haselby, Battle Ground, IN (US); Sara M. Sherman, Lafayette, IN (US); Charles Baxter, West Lafayette, IN (US); Richard Hadley, Otterbein, IN (US); Keith Milner, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 142 days.

This patent is subject to a terminal disclaimer.

(21) Appl. No.: 15/065,502

(22) Filed: Mar. 9, 2016

(65) Prior Publication Data

US 2016/0183969 A1 Jun. 30, 2016

Related U.S. Application Data (63) Continuation of application No. 14/196,812, filed on Mar. 4, 2014, now Pat. No. 9,308,020.

(60) Provisional application No. 61/782,572, filed on Mar. 14, 2013.

(51) Int. Cl.
*A61B 17/34* (2006.01)
*A61M 25/06* (2006.01)

(52) U.S. Cl.
CPC ...... *A61B 17/3417* (2013.01); *A61B 17/3403* (2013.01); *A61M 25/06* (2013.01); *A61B 2017/3454* (2013.01)

(58) Field of Classification Search
CPC ............. A61B 17/3417; A61B 10/025; A61B 17/06066; A61B 17/34
USPC .......................... 606/167, 185, 223; 604/264
See application file for complete search history.

(56) References Cited

U.S. PATENT DOCUMENTS

| | | | |
|---|---|---|---|
| 1,599,059 A * | 9/1926 | Morton | A61B 17/06066 223/102 |
| 3,090,384 A * | 5/1963 | Baldwin | A61M 5/3286 604/272 |
| 3,308,822 A | 3/1967 | De Luca | |
| 4,411,657 A | 10/1983 | Galindo | |
| 4,838,877 A | 6/1989 | Massau | |
| 5,219,358 A | 6/1993 | Bendel et al. | |
| 5,290,249 A | 3/1994 | Foster et al. | |
| 5,385,572 A | 1/1995 | Nobles et al. | |
| 5,389,077 A | 2/1995 | Melinyshyn et al. | |
| 5,403,344 A | 4/1995 | Allen | |
| 5,522,833 A | 6/1996 | Stephens et al. | |

(Continued)

*Primary Examiner* — Katherine M Shi
(74) *Attorney, Agent, or Firm* — Brinks Gilson & Lione (57) ABSTRACT A needle disclosed herein may include an elongate body extending between a proximal end and a distal end with a central longitudinal axis defined by the body, where the distal end includes a single sharp point along the central longitudinal axis and defining a distal end terminus three longitudinal fluted surfaces converging at the distal end terminus; and three longitudinal beveled cutting edges defining borders between the fluted surfaces and converging at the distal end terminus. Needle embodiments may include one or more ports open into and/or proximal of the fluted surfaces and communicating with one or more longitudinal needle lumens.

20 Claims, 6 Drawing Sheets (56) References Cited

U.S. PATENT DOCUMENTS

| | | | |
|---|---|---|---|
| 5,527,335 A | | 6/1996 | Bolduc et al. |
| 5,626,598 A | | 5/1997 | Roth |
| 5,674,237 A | | 10/1997 | Ott |
| 5,792,123 A | | 8/1998 | Ensminger |
| 5,848,996 A | * | 12/1998 | Eldor ................ A61B 17/3401 604/164.11 |
| 6,007,544 A | | 12/1999 | Kim |
| 2001/0049503 A1 | | 12/2001 | Estabrook et al. |
| 2003/0233114 A1 | | 12/2003 | Merboth et al. |
| 2004/0098048 A1 | | 5/2004 | Cunningham et al. |
| 2005/0171504 A1 | | 8/2005 | Miller |
| 2008/0300617 A1 | | 12/2008 | Smith |
| 2009/0124859 A1 | | 5/2009 | Assell et al. |
| 2010/0016811 A1 | | 1/2010 | Smith |
| 2012/0220145 A1 | | 8/2012 | Chang |
| 2012/0221007 A1 | | 8/2012 | Batten et al. |
| 2012/0316595 A1 | | 12/2012 | Kahle et al. |
| 2015/0142038 A1 | * | 5/2015 | Melsheimer ....... A61B 17/3421 606/185 |

* cited by examiner

TRI-FLUTED VASCULAR ACCESS NEEDLE

CROSS-REFERENCE TO RELATED APPLICATIONS

This application is a Continuation under 35 U.S.C. § 120 of U.S. application Ser. No. 14/196,812, filed Mar. 4, 2014, which claims priority to U.S. provisional application Ser. No. 61/782,572, filed Mar. 14, 2013, each of which is incorporated by reference herein in its entirety.

TECHNICAL FIELD

Embodiments disclosed herein generally relate to medical needles. More particularly the embodiments disclosed relate to vascular access needles.

BACKGROUND

Minimally invasive treatments including endovascular therapies are increasing preferred and used instead of traditional "open surgical" interventions whenever possible. Endovascular techniques may be used to diagnose and/or treat a broad range of pathologies. Therapies may range from critical limb ischemia and aneurysm repair to ischemic stroke therapies and treatment of vascular stenoses. All endovascular techniques require a vascular access site for device introduction into a vascular lumen. For treatment personnel (e.g., surgeons and those assisting them), choosing the best site for an initial puncture and the best path for the introduction of devices poses a challenge for any endovascular procedure. Vascular access requires a complex balance of entry into and closure of a vascular entry site, most preferably with a minimum of discomfort and postoperative risk to the patient being treated.

Examples of access procedures may include, but are not limited to, central line placements (e.g., power ports, peripherally inserted central catheters (PICCS), dialysis/pheresis catheters), arterial access, peritoneal access, spinal access, and venous access. For example, the maintenance and longevity of vascular access remains one of the most problematic topics in the care of dialysis patients. Although much attention has focused on neointimal hyperplasia, the repetitive trauma to vessel walls by dialysis needles causes significant cumulative damage that has not been broadly investigated. Commercial needles have beveled tips with intentional cutting surfaces to ease manual insertion. Several complications may arise, particularly with repeated vascular access, including—for example—hematoma formation, clotting, aneurysm, and infections at the cannulation sites.

Several approaches attempt to avoid these complications. Examples of these include the "ladder approach" where consecutive dialysis puncture sites are successively and systematically located a small distance away from each prior dialysis puncture site, allowing the previous sites to heal. After a time the previous sites are reused. Another technique uses a region for repeated punctures. This often results in local aneurysmal dilation at or near the puncture site of the vessel. Another approach utilizes the precise placement of the needle in the same spot as close as possible, repeatedly using—as nearly as possible—the same insertion site, depth, and angle. This approach, known as the "button-hole" technique appears to lead to the longest lasting use of an arteriovenous (AV) fistula type of dialysis. Similar complications may arise from single-access procedures such as, for example, femoral access for cardiac stent placement, where the access site may be at risk of hematoma formation or infection. These risks may be reduced by minimizing the amount of time required for the body to seal the blood vessel wall after a procedure (and, by extension, between successive procedures).

Accordingly it is desirable to provide a vascular access needle that causes minimal trauma to a penetration site, from which the patient's body may more rapidly heal.

BRIEF SUMMARY

In one aspect, a needle disclosed herein may include an elongate body extending between a proximal end and a distal end with a central longitudinal axis defined by the body, where the distal end includes a single sharp point along the central longitudinal axis and defining a distal end terminus three longitudinal fluted surfaces converging at the distal end terminus; and three longitudinal beveled cutting edges defining borders between the fluted surfaces and converging at the distal end terminus.

DETAILED DESCRIPTION

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

A tri-fluted vascular access needle is provided that may also be used for other diagnostic or therapeutic purposes. Its novel penetrating tip structure provides for minimally-traumatic penetration through tissue in a manner that provides for rapid healing. This may be particularly useful for persons who have to be subjected to repeated needle-access procedures (e.g., hemodialysis), as the presently-described embodiments provide for faster closure and hemostasis at an access site than existing needles.

The invention is defined by the claims, may be embodied in many different forms, and should not be construed as limited to the embodiments illustrated herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

The terms "proximal" and "distal" are used herein in the common usage sense where they refer respectively to a handle/doctor-end of a device or related object and a tool/patient-end of a device or related object.

Figures 1A, 1B:
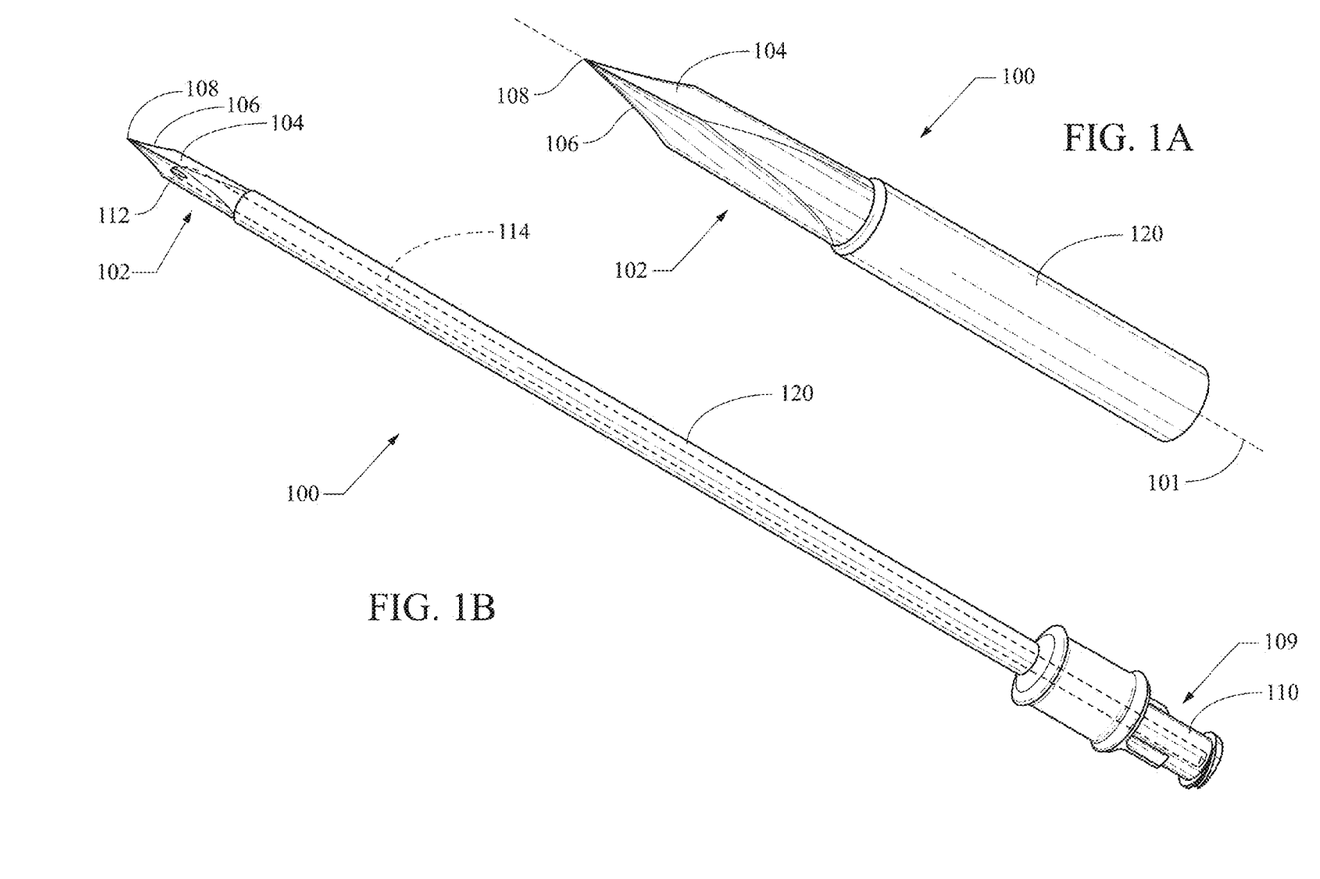
FIGS. 1A-1B show, respectively, a distal end portion of a tri-fluted needle embodiment and a tri-fluted needle embodiment with a proximal cannula.

One embodiment of a tri-fluted needle 100 is described with reference to FIGS. 1A and 1B. FIG. 1A shows the distal end portion of the tri-fluted needle 100. The needle 100 includes a distal end body 102 that preferably is constructed of a metal alloy. Stainless steel and tungsten carbide may be used as the metal alloy in certain embodiments. The distal end body construction 102 may include ceramic material, ceramic-metal composite, and/or appropriate rigid polymeric material (e.g., polyetheretherketone/PEEK) instead of or in addition to the metal alloy. A generally cylindrical cannula 120 extends proximally from the distal end body 102, to a proximal end 109 of the device, shown in FIG. 1B as including a hub 110. The cannula 120 may be substantially rigid and inflexible to provide sufficient rigidity for controllable, predictable straightline operation in penetrating through tissue. Metal, polymer, and other construction materials used or developed in the art may be used for cannula construction, which may—as illustrated in the drawings of some embodiments—include a smaller outer perimeter than the body (e.g., reference line 202 of FIG. 2C). In other embodiments, the cannula 120 may be flexible (e.g., sufficiently flexible to coil within a 6 cm-diameter circle).

The needle 100 is generally symmetrically constructed around a central longitudinal axis indicated in FIG. 1A by a phantom line 101. The distal body 102 includes three longitudinal fluted surfaces 104, the adjoining borders of which form three longitudinal beveled cutting edges 106. The three longitudinal fluted surfaces 104 and the three longitudinal beveled cutting edges 106 converge at a distal end terminus 106 to form a sharp point, which is congruent with the central longitudinal axis. As shown in FIG. 1B, the body 102 may include a port 112 disposed in one of the flutes 104 and providing communication with a longitudinal lumen 114 extending through the body 102 and cannula 120.

Figure 2A:
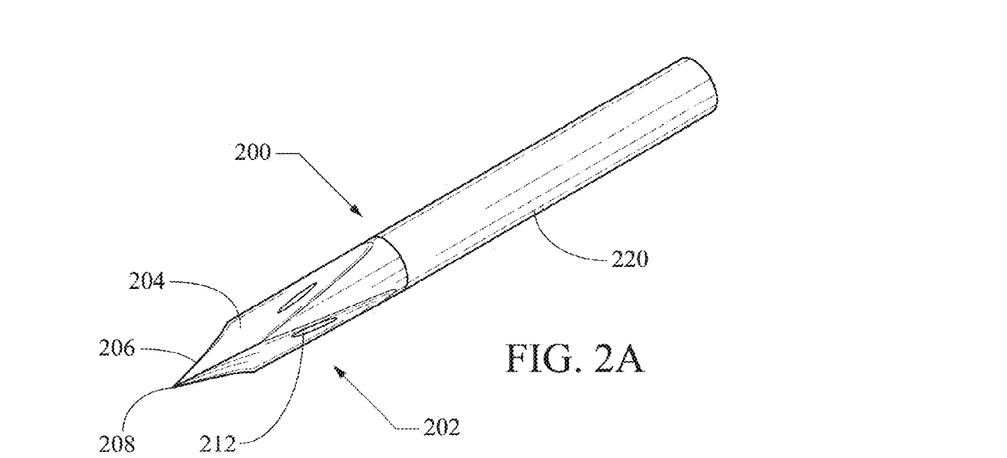
FIGS. 2A-2E show, respectively, perspective and end views of a tri-fluted needle embodiment.
Figure 2B:
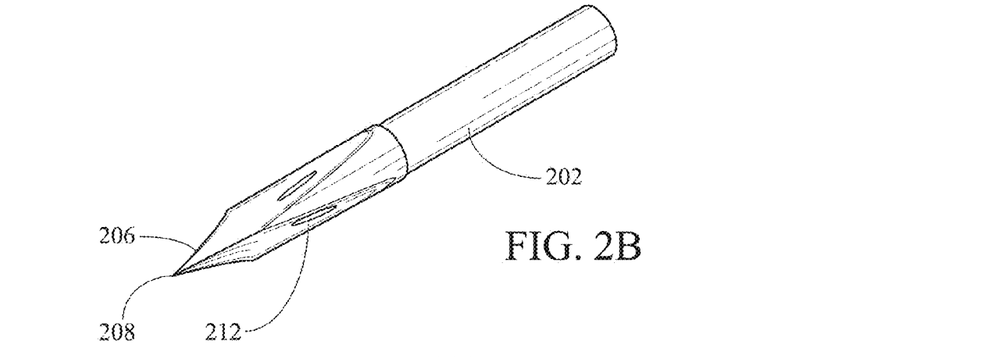
Figure 2C:
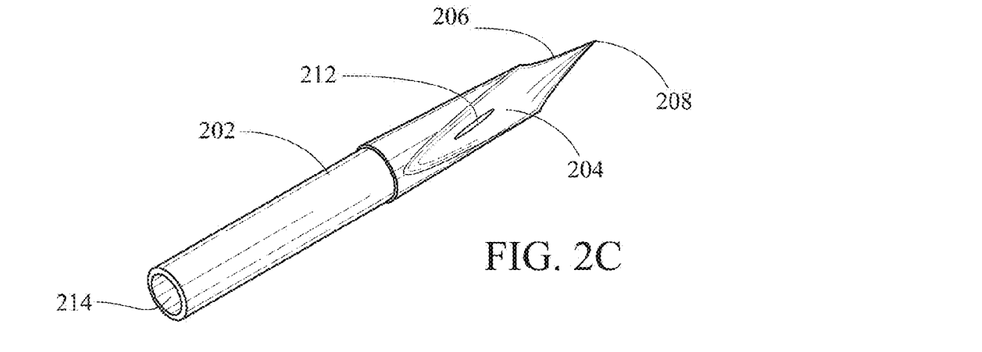
Figure 2D:
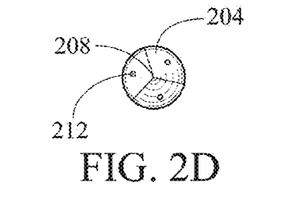
Figure 2E:
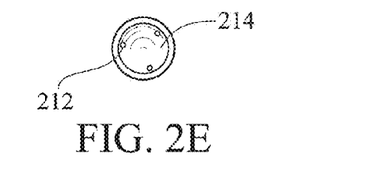

A second needle embodiment 200 is shown in FIGS. 2A-2E. FIG. 2A shows the distal end portion of the tri-fluted needle 200 with a cannula 220 extending proximally from the needle body 202. FIGS. 2B-2E show the distal needle body 202 without the cannula 220. FIG. 2B shows the same perspective view as FIG. 2A, except without the cannula 220 overlying and extending proximally from a base portion of the distal needle body 202. FIG. 2C shows an opposite side view from FIGS. 2A-2B. FIG. 2D shows a distal-end elevation view including all three flutes 204 and ports 212, and FIG. 2E shows a proximal-end-view, of the distal body 202, including the lumen 214. The distal-end view of FIG. 2D shows that the cutting edges are oriented at about 120° relative to each other around the circumference of the cylindrical needle body 202.

The distal body 202 includes three longitudinal fluted surfaces 204, the adjoining borders of which form three longitudinal beveled cutting edges 206. The three longitudinal fluted surfaces 204 and the three longitudinal beveled cutting edges 206 converge at a distal end terminus 208 to form a sharp point, which is congruent with the radially central longitudinal axis (as clearly shown in FIG. 2D with reference also to at least FIGS. 1A and 3C, where radially central includes being exactly radially centered). The body 202 may include a plurality of circular-section ports 212 (like the single port 112 in FIG. 1B), with one disposed in each of the flutes 204 and providing communication with a longitudinal lumen 214 extending through the body 202 and cannula 220. The ports 212 are oriented parallel with the central longitudinal axis. It should be appreciated that the lumen 214 could be configured as a plurality of lumens that allow or prevent communication therebetween, where those of skill in the art will appreciate that each of such a plurality of lumens may communicate with one or more of the ports 212.

Figure 3A:
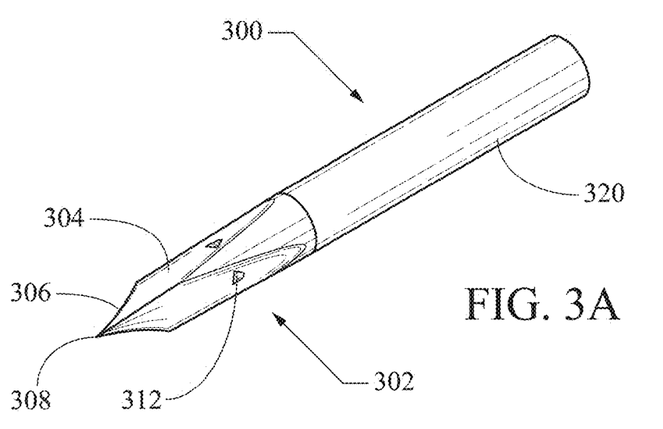
FIGS. 3A-3D show, respectively, perspective and end views of a tri-fluted needle embodiment.
Figure 3B:
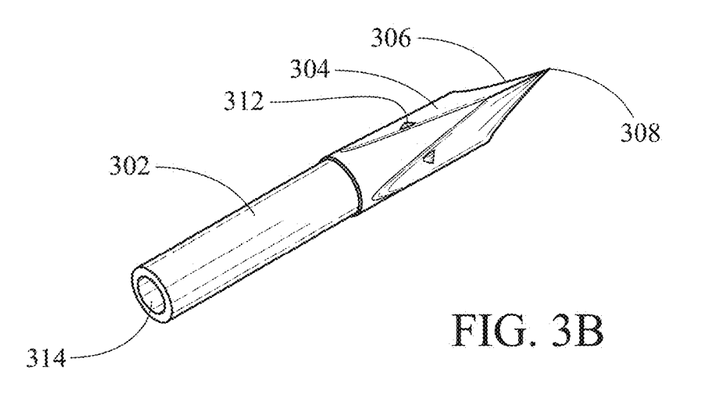
Figure 3C:
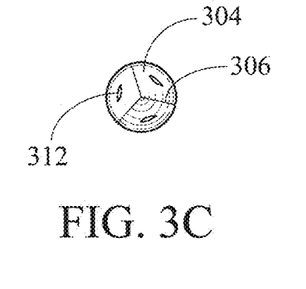
Figure 3D:
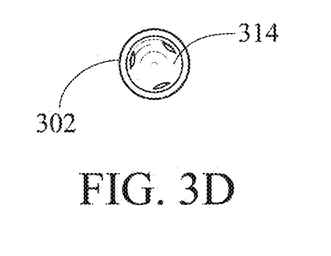

A third needle embodiment 300 is shown in FIGS. 3A-3D. FIG. 3A shows the distal end portion of the tri-fluted needle 300 with a cannula 320 extending proximally from the needle body 302. FIGS. 3B-3D show the distal needle body 302 without the cannula 320. FIG. 3B shows the same perspective view as FIG. 3A, except without the cannula 320 overlying and extending proximally from a base portion of the distal needle body 302. FIG. 3C shows a distal end elevation view, and FIG. 3D shows a proximal end-view, of the distal body 302.

The distal body 302 includes three longitudinal fluted surfaces 304, the adjoining borders of which form three longitudinal beveled cutting edges 306. The three longitudinal fluted surfaces 304 and the three longitudinal beveled cutting edges 306 converge at a distal end terminus 308 to form a sharp point, which is congruent with the central longitudinal axis. The body 302 may include a plurality of semicircular-section ports 312, with one disposed in each of the flutes 304 and providing communication with a longitudinal lumen 314 extending through the body 302 and cannula 320. It should be appreciated that the lumen 314 could be configured as a plurality of lumens that allow or prevent communication therebetween, where those of skill in the art will appreciate that each of such a plurality of lumens may communicate with one or more of the ports 312. The ports 312 are oriented parallel with the central longitudinal axis.

Figure 4:
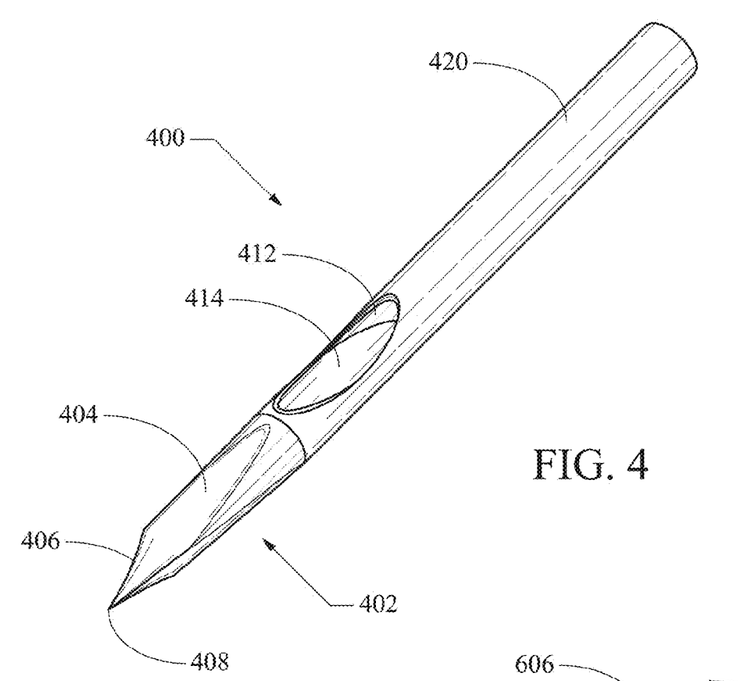
FIG. 4 shows a tri-fluted needle embodiment with a side port for a wire guide.

A fourth needle embodiment 400 is shown in FIG. 4. FIG. 4 shows the distal end portion of the tri-fluted needle 400 with a cannula 420 extending proximally from the needle body 402. The distal body 402 includes three longitudinal fluted surfaces 404, the adjoining borders of which form three longitudinal beveled cutting edges 406. The three longitudinal fluted surfaces 404 and the three longitudinal beveled cutting edges 406 converge at a distal end terminus 408 to form a sharp point, which is congruent with the central longitudinal axis. The body 402 may include a wire guide port 414 proximal of the tapering distal end that includes the flutes 404 and edges 406. The wire guide port 414 provides communication with a longitudinal wire guide lumen 412 extending through the body 402 and cannula 420. This structure will allow the needle 400 to be used for providing access for a wire guide, and/or for the needle 400 to be directed along a wire guide.

Needle construction, including some methods for making a needle in keeping with the present disclosure, is discussed with reference to FIGS. 5A-5C, which illustrate three embodiments of a needle body 502. The body 502 includes three longitudinal fluted surfaces 504, the adjoining borders of which form three longitudinal beveled cutting edges 506. The three longitudinal fluted surfaces 504 and the three longitudinal beveled cutting edges 506 converge at a distal end terminus 508 to form a sharp point, which is congruent with the central longitudinal axis.

Figure 5A:
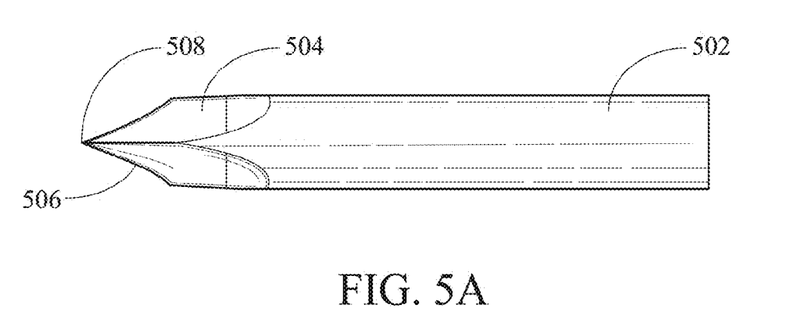
FIGS. 5A-5C show different needle body cutting edge configurations.
Figure 5B:
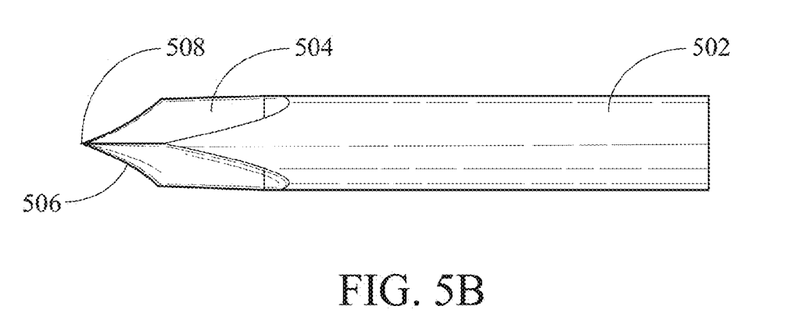
Figure 5C:
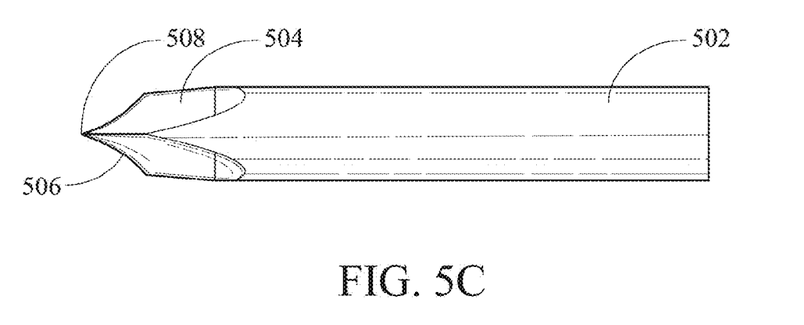

In FIG. 5A, one example of a needle body embodiment 502 includes beveled cutting edges 506, each of which is radially separated from the other edges 506 by about 120°. Each of the beveled cutting edges 506 is about 2.7 mm in length (where the length is straightline linear distance from the sharply-pointed distal terminus 508 to a point congruent with the outermost needle body circumference), and the outer diameter is about 2.1 mm. The distalmost length of each beveled cutting edge 506 is oriented at an angle of about 8° relative to the central longitudinal axis but curves slightly to a steeper relative angle as it nears and merges with the outer circumference of the body 502. In FIG. 5B, another example of a needle body embodiment 502 includes beveled cutting edges 506, each of which is radially separated from the other edges 506 by about 120°. Each of the beveled cutting edges 506 is about 2 mm in length), and the outer diameter is about 2.1 mm. The distalmost length of each beveled cutting edge 506 is oriented at an angle of about 12° relative to the central longitudinal axis but curves slightly to a steeper relative angle as it nears and merges with the outer circumference of the body 502. And, in FIG. 5C, another example of a needle body embodiment 502 includes beveled cutting edges 506, each of which is radially separated from the other edges 506 by about 120°. Each of the beveled cutting edges 506 is about 1.8 mm in length. The distalmost length of each beveled cutting edge 506 is oriented at an angle of about 8° relative to the central longitudinal axis but curves slightly to a steeper relative angle as it nears and merges with the outer circumference of the body 502. In preferred embodiments, the cutting edge angle may vary from about 7° to about 15°. Needles incorporating the presently-disclosed novel tri-fluted tip may range in size from about 30 Fr (<10-gauge) to 1 Fr (29-gauge).

Those of skill in the arts of medical device manufacture and/or metal tooling will appreciate that this tri-fluted configuration can be made by providing a cylindrical cannula body 502 that may be solid, or that may include one or more generally longitudinal lumens. A ball-tipped, cylindrical-body milling tool can be applied to the cannula at an angle intersecting the distal end terminus at the central longitudinal axis to form each of the three longitudinal fluted surfaces 504 by removing cannula body material. When executed consistently around the cannula (whether symmetrically or asymmetrically), the resulting tip provides the tri-fluted configuration with three cutting edges described herein.

In certain embodiments, a desired configuration can be achieved by use of a formula during manufacture where a radius defined by the proximal curved end of a fluted surface between adjacent beveled cutting edges is equal in length to four times the needle body outer diameter, with a desired degree angle (e.g., about 3° to about 15°, with a preferred angle of about 7°). As such, each of the fluted surfaces forms a partial conical surface.

Figure 6:
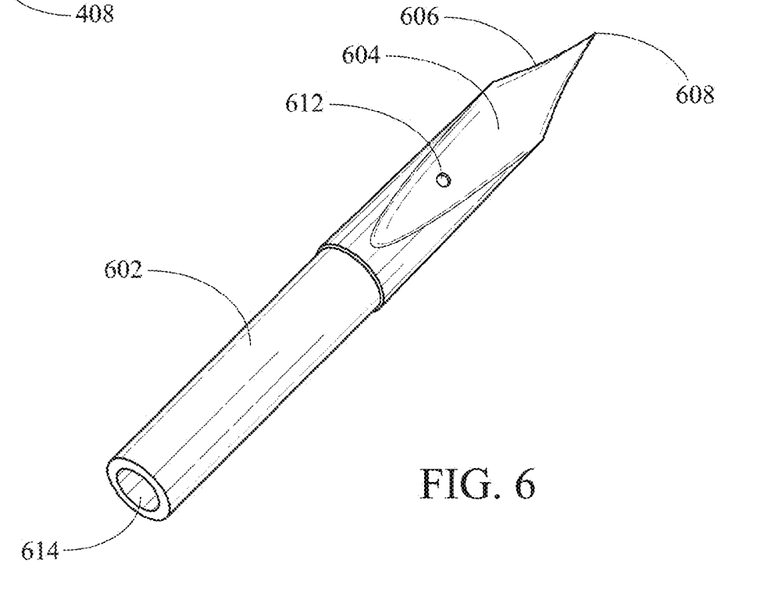
FIG. 6 shows another tri-fluted needle embodiment.

FIG. 6 shows the distal end portion of another embodiment of a tri-fluted needle including a needle body 602 (shown without a cannula). The body 602 includes three longitudinal fluted surfaces 604, the adjoining borders of which form three longitudinal beveled cutting edges 606. The three longitudinal fluted surfaces 604 and the three longitudinal beveled cutting edges 606 converge at a distal end terminus 608 to form a sharp point, which is congruent with the central longitudinal axis. The body 602 may include a circular port 612, disposed in through one of the flutes 604 and providing communication with a longitudinal lumen 614 extending through the body 602. The circular port 612 is oriented perpendicular to the central longitudinal axis. It should be appreciated that these and other port configurations may vary in size, shape, number, and orientation (e.g., relative in angle to the central longitudinal axis and relative to other needle body features).

The inventors were pleasantly surprised to find the efficacy of the present needle configuration as applied to piercing through tissue and particularly as used for vascular access. For example, a 23-gauge vascular access embodiment of the presently-disclosed tri-fluted needle was compared with a standard 23-gauge lancet-beveled vascular access needle for femoral access in an ovine model. Hemostasis was achieved in one-half the time with the presently-disclosed tri-fluted needle as compared to the same-sized needle with a standard lancet bevel. The same result was observed when comparing two 18-gauge needles, where one included the present novel tri-fluted configuration and the other included a lancet bevel tip.

Figure 7A:
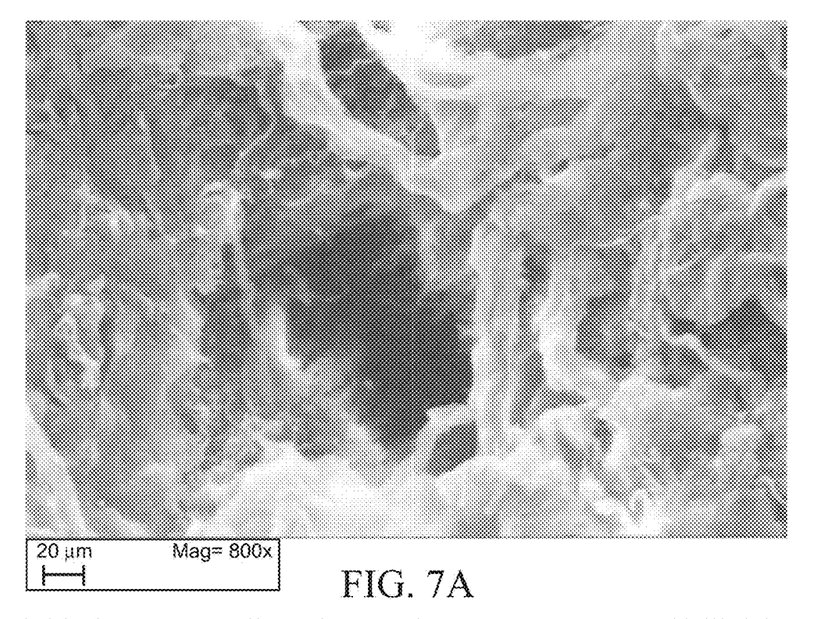
FIGS. 7A and 7B are SEM micrographs of tissue, contrasting penetration of a prior art needle and the presently-disclosed needle.
Figure 7B:
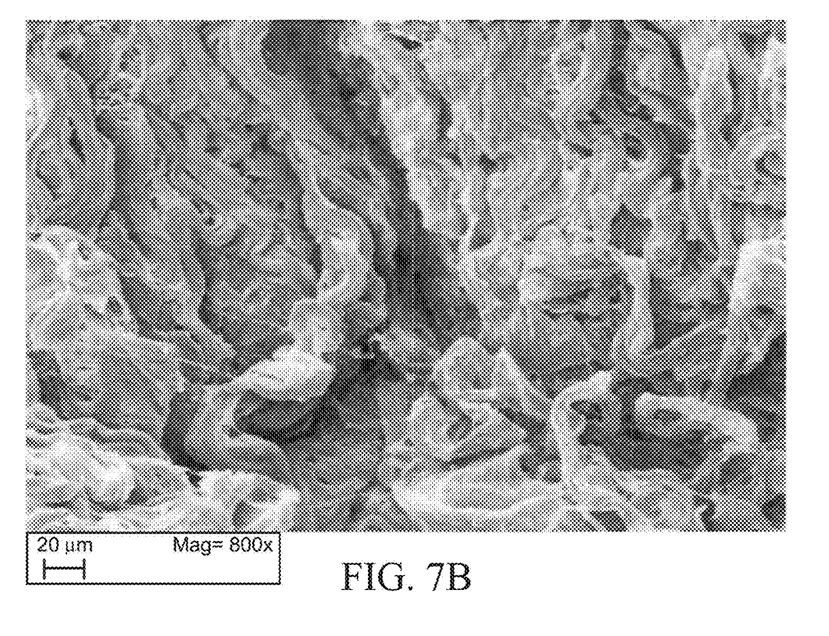

FIGS. 7A and 7B show scanning electron micrographs of puncture sites in porcine arterial vessels. FIG. 7A shows the puncture made by a standard lancet-bevel needle (at 800× magnification), and FIG. 7B shows the puncture made by the presently-disclosed tri-fluted needle (at 800× magnification). Those of skill in the art will appreciate that the improved speed of hemostasis may be due in part to the body's natural healing response to tissue disruption by a needle and the provision of a "tri-cuspid valve-like" puncture wound (FIG. 7B) that leaves immediately-adjacent tissue edges that can readily be knit back together by the body's natural hemostasis mechanisms in a more rapid manner than a circular or semicircular aperture left by a lancet-bevel (FIG. 7A), where the gap between tissue edges slows hemostasis and healing.

This improved rapidity in hemostasis and healing, attributable to the present novel design, also provides reduced occurrence and reduced severity of hematoma in endovascular procedures (e.g., where the femoral artery is punctured to provide access for an endovascular procedure via Seldinger technique). Additionally, it will reduce the likelihood or at least the prevalence of scarring and/or tissue thinning associated with multiple punctures in a given location such as described above with reference to buttonhole procedures accessing an A-V fistula. Preserving access site cannulation ability for repeated hemodialysis will improve patient care and reduce the likelihood of infection and thinning skin. As such, the present novel needle design provides redress for problems associated with these common medical procedures.

Each of the illustrated embodiments has been shown with symmetrical flutes and cutting edges, but those of skill in the art will appreciate that the three flutes and intervening three cutting edges may vary from each other in size and shape within the confines of a needle geometry while remaining within the scope of the present disclosure. That is, those of skill in the art will be able (with reference to the present teaching) to provide other embodiments that vary the size/proportion of the flutes and cutting edges.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment.

We claim:

1. A vascular access needle, comprising:
an elongate body extending between a proximal end and a distal end; and
a radially central longitudinal axis defined by the body;
where the distal end includes a tissue penetrating portion consisting of:
a single sharp point along the central longitudinal axis and defining a radially-centered distal end terminus;
three longitudinal flutes converging at the distal end terminus, including at least one port open from at least one of the three longitudinal flutes to a needle lumen; and
three longitudinal beveled cutting edges defining borders between the flutes and converging at the radially-centered distal end terminus.

2. The vascular access needle of claim 1, where the three longitudinal flutes are all symmetrical to each other.

3. The vascular access needle of claim 1, where the three longitudinal beveled cutting edges are all symmetrical to each other.

4. The vascular access needle of claim 1, wherein at least a first port of the at least one port open from at least one of the three longitudinal flutes to a needle lumen, is oriented perpendicular to the radially central longitudinal axis.

5. The vascular access needle of claim 1, wherein at least a first port of the at least one port has a cross-section—in a plane that is perpendicular to the radially central longitudinal axis—that is circular or that is semicircular.

6. The vascular access needle of claim 1, where at least one of the three longitudinal beveled cutting edges includes a coated metal construction.

7. The vascular access needle of claim 6, where the coating includes ceramic, polymer, or any combination thereof.

8. The vascular access needle of claim 1, where the body is constructed from stainless steel, tungsten carbide, polyetheretherketone, or any combination thereof.

9. The vascular access needle of claim 1, where the body comprises a metal construction, and a generally cylindrical cannula extends from the proximal end of the body, where the cannula includes at least one lengthwise portion having a smaller outer perimeter than an outer perimeter of the distal metallic body.

10. The vascular access needle of claim 9, where the generally cylindrical cannula is substantially rigid and inflexible.

11. The vascular access needle of claim 9, where the generally cylindrical cannula is sufficiently flexible to coil within a 6 cm-diameter circle.

12. The vascular access needle of claim 9, where the generally cylindrical cannula comprises metallic construction, polymer construction, or any combination thereof.

13. A vascular access needle, comprising:
an elongate body extending between a proximal end and a distal end; and
a radially central longitudinal axis defined by the body;
where the distal end includes a tissue penetrating portion consisting of:
a single sharp point along the central longitudinal axis and defining a radially-centered distal end terminus;
three longitudinal flutes converging at the distal end terminus; and
three longitudinal beveled cutting edges defining borders between the flutes and converging at the radially-centered distal end terminus; and
at least one port open from each of the three longitudinal flutes to a needle lumen.

14. The vascular access needle of claim 13, where the at least one port open from each of the three longitudinal flutes to a needle lumen is parallel with each other at least one port.

15. The vascular access needle of claim 14, where the at least one port is also parallel with the radially central longitudinal axis.

16. A needle, comprising:
a distal metallic body extending from a sharply pointed distal terminus;
a radially central longitudinal axis defined by the body;
where the distal terminus is disposed along the central longitudinal axis and consists of a radially-centered convergence of
three longitudinal flutes, including at least a first port open from a first one of the three longitudinal flutes to a first needle lumen, and
three longitudinal beveled cutting edges defining borders between the three longitudinal flutes;
where the three longitudinal beveled cutting edges each include a distalmost angle relative to the central longitudinal axis of about 7° to about 15°; and
a cannula extending from a proximal end of the distal metallic body.

17. The vascular access needle of claim 16, where the cannula comprises metallic construction, polymer construction, or any combination thereof, and includes at least one lengthwise portion having a smaller outer perimeter than an outer perimeter of the distal metallic body.

18. The vascular access needle of claim 16, further comprising at least one port open from each of the three longitudinal flutes to a needle lumen.

19. The vascular access needle of claim 18, where the at least one port open from each of the three longitudinal flutes to a needle lumen is parallel with each other at least one port.

20. The vascular access needle of claim 16, further comprising at least a second port open from a second of the three longitudinal flutes to a second needle lumen.

* * * * *